US00PP24995P3

(12) United States Plant Patent
Stewart

(10) Patent No.: US PP24,995 P3
(45) Date of Patent: Oct. 21, 2014

(54) ***ANIGOZANTHOS* PLANT NAMED 'RAMBOTASY'**

(50) Latin Name: ***Anigozanthos* hybrid**
Varietal Denomination: Rambotasy

(71) Applicant: Ian Angus Stewart, Somersby (AU)

(72) Inventor: Ian Angus Stewart, Somersby (AU)

(73) Assignee: Ramm Botanical Holdings (AU)

( * ) Notice: Subject to any disclaimer, the term of this patent is extended or adjusted under 35 U.S.C. 154(b) by 0 days.

(21) Appl. No.: 13/815,095

(22) Filed: Jan. 30, 2013

(65) Prior Publication Data

US 2014/0215664 P1 Jul. 31, 2014

(51) Int. Cl.
*A01H 5/00* (2006.01)

(52) U.S. Cl.
USPC ..... Plt./362

(58) Field of Classification Search
USPC ..... Plt./362
See application file for complete search history.

*Primary Examiner* — Annette Para
(74) *Attorney, Agent, or Firm* — Cassandra Bright

(57) ABSTRACT

A new and distinct *Anigozanthos* cultivar named 'AJJYE03-0' is disclosed, characterized by a short compact plant form, yellow flowers, well branched flowering stems and year round flowering. The new variety also has a compact, ball-shaped, well branched growth habit. The new variety is an *Anigozanthos*, normally produced as an outdoor garden or container plant.

2 Drawing Sheets

Figure 1:
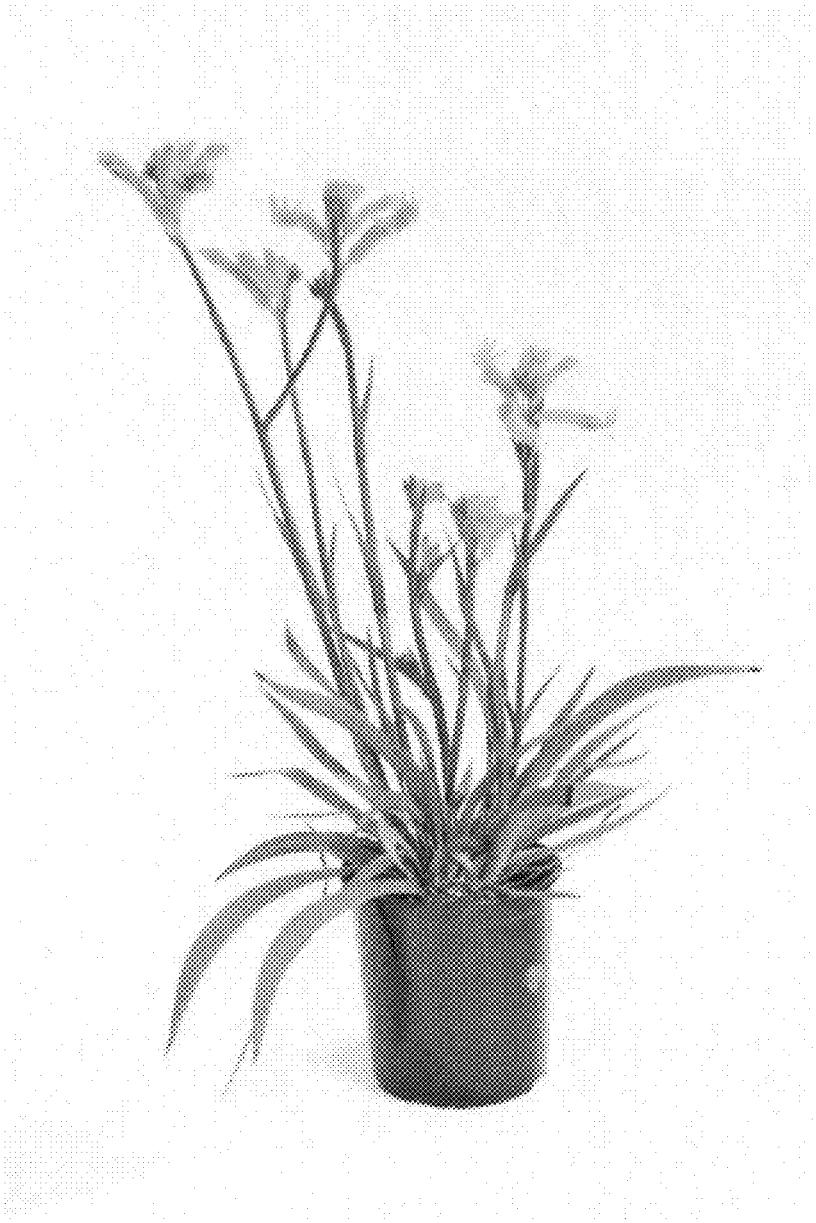

Latin name of the genus and species: *Anigozanthos* hybrid.
Variety denomination: 'Rambotasy'.

BACKGROUND OF THE INVENTION

The new *Anigozanthos* cultivar is a product of a planned breeding program conducted by the inventor, Ian Angus Stewart, in Kangy Angy, Australia. The objective of the breeding program was to produce new *Anigozanthos* varieties for ornamental commercial applications. The cross resulting in this new variety was made Sep. 21, 2007.

The seed parent is the unpatented proprietary variety referred to as *Anigozanthos* hybrid 'A06-0218'. The pollen parent is the unpatented proprietary variety referred to as *Anigozanthos* hybrid 'A06-0169'. The new variety was discovered Aug. 24, 2008, by the inventor in a group of seedlings resulting from the September 2007 crossing, in a research greenhouse in Kangy Angy, Australia.

Asexual reproduction of the new cultivar was performed by tissue culture. This was first performed at a laboratory in Kangy Angy, Australia during 2008 and has shown that the unique features of this cultivar are stable and reproduced true to type over several successive generations.

SUMMARY OF THE INVENTION

The cultivar 'Rambotasy' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Rambotasy'. These characteristics in combination distinguish 'Rambotasy' as a new and distinct *Anigozanthos* cultivar:

1. Short plant height
2. Compact and very well branched plant
3. Bright yellow flowers 4. Branched flower stems
5. Year round flowering.

PARENT COMPARISON

Plants of the new cultivar 'Rambotasy' are similar to plants of the seed parent, *Anigozanthos* hybrid 'A06-0218' in most horticultural characteristics, however, plants of the new cultivar 'Rambotasy' are easier to propagate in tissue culture. Additionally, plants of the new variety produce a different ovary color than the seed parent.

Plants of the new cultivar 'Rambotasy' are similar to plants of the pollen parent; *Anigozanthos* hybrid 'A06-0169' in most horticultural characteristics, however, plants of the new cultivar 'Rambotasy' produce inflorescence of primary ramification, whereas the pollen parent produces inflorescences with tertiary ramification. 'Rambotasy' also produces a different color ovary than the pollen parent.

COMMERCIAL COMPARISON

Plants of the new cultivar 'AJJYE03-0' are comparable to the variety *Anigozanthos* 'Rambubona' U.S. Plant Pat. No. 18,207. The two *Anigozanthos* varieties are similar in most horticultural characteristics; however, the new variety 'Rambotasy' differs in having a narrower leaf and less flowers per inflorescence. Additionally, plants of 'Rambotasy' produce flowers primarily colored Yellow-Orange 17A, whereas plants of 'Rambubona' produce flowers colored primarily Yellow-Orange 14B. Plants of 'Rambotasy' produce pedicels, ovaries and perianth tubes colored with red hairs, whereas hairs found on the same floral parts of 'Rambubona' are colored yellow.

Plants of the new cultivar 'Rambotasy' can also be compared to the commercial variety *Anigozanthos* 'Bush Tenacity', unpatented. These varieties are similar inmost horticultural characteristics; however 'Bush Tenacity' produces narrower, more glaucous leaves than 'Rambotasy'. Foliage of 'Rambotasy' is less prone to leaf blackening than 'Bush Tenacity'. Additionally, inflorescences of 'Rambotasy' are branched, whereas inflorescences of 'Bush Tenacity' are unbranched.

BRIEF DESCRIPTION OF THE PHOTOGRAPHS

The accompanying photograph in FIG. 1 illustrates in full color a typical plant of 'Rambotasy' grown in a greenhouse, in a 15 cm pot. Age of the plant photographed is approximately 1 year from a rooted plantlet.

Figure 2:
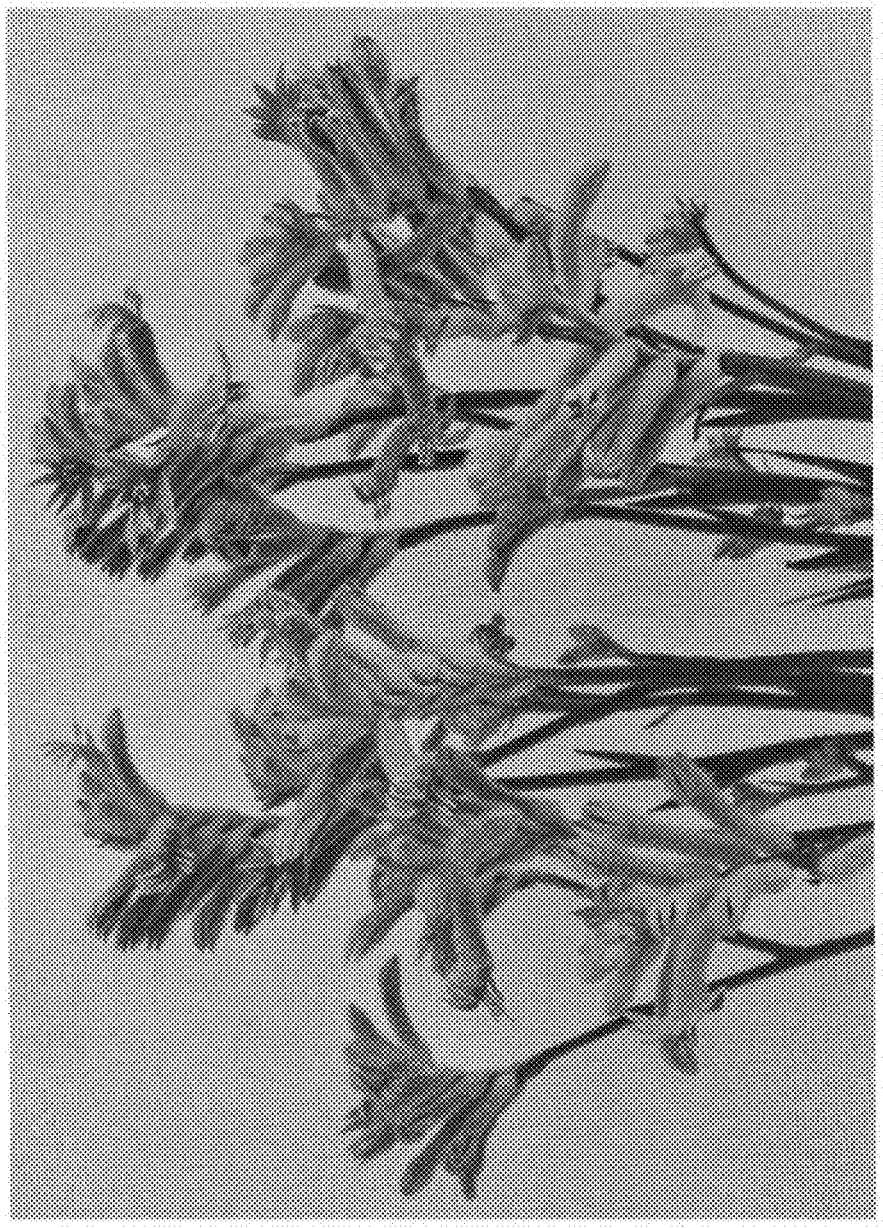

FIG. 2 illustrates in full color a close up of a typical bloom of 'Rambotasy'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'Rambotasy' plants grown in a greenhouse, in Santa Paula, Calif. The growing temperature ranged from 20° C. to 35° C. during the day and from 17° C. to 23° C. during the night. General light conditions are bright, normal sunlight. Measurements and numerical values represent averages of typical plant types.

Botanical classification: *Anigozanthos* hybrid 'Rambotasy'.

PROPAGATION

Typically propagated by micropropagation tissue culture. A tissue culture plantlet is typically rooted in 1 to 2 weeks at approximately 25° C.

Root description: Root description: Thick, fleshy main roots with fibrous network of much smaller roots.

PLANT

Age of plant described: Approximately 1 year from a rooted cutting.

Growth habit: Upright fan shaped perennial with basal only branching.

Pot size of plant described: Commercial 1 quarter size container.

Height:

*Top of foliar plane.*—20 to 25 cm.

*Top of flowering plane.*—45 to 50 cm.

Plant spread: 30 to 35 cm.

Growth rate: Moderate.

FOLIAGE

Leaf:

*Arrangement.*—Basally emerging, irregular rosette. Primarily fan-shaped.

*Quantity.*—Approximately 25 leaves on a 1 year old plant.

*Average length.*—Approximately 20 cm.

*Average width.*—Approximately 1.6 cm.

*Shape of blade.*—Subulate.

*Apex.*—Acuminate.

*Base.*—Clasping.

*Attachment.*—Sessile.

*Margin.*—Entire.

*Texture of top surface.*—Glabrous, ridged.

*Texture of lower surface.*—Glabrous, ridged.

*Color.*—Young foliage upper side: Near RHS Green 137B. Young foliage under side: Near RHS Green 137B. Mature foliage upper side: Near RHS Green 137B. Mature foliage under side: Near RHS Green 137B.

*Venation.*—Type: Pinnate. Venation color upper side: Near RHS Green 137B. Venation color under side: Near RHS Green 137B.

*Petiole.*—Not Present.

FLOWER

Natural flowering season: Freely flowering under outdoors growing conditions with substantially continuous blooming from spring through autumn.

Inflorescence and flower type and habit: Large flowers arranged singly on terminal and axillary racemes. Inflorescence have primary ramification. Individual flowers are zygomorphic, tubular, with a curved perianth.

Inflorescence height: Approximately 10 cm.

Inflorescence width: Approximately 8 cm.

Flower longevity on plant: Individual flowers last approximately 30 days.

Approximate quantity of flowers per plant: About 40 flowers and buds per plant.

Persistent or self-cleaning: Persistent.

Bud:

*Shape.*—Tubular.

*Length.*—About 3.5 cm.

*Diameter.*—About 0.7 cm.

*Texture.*—Pilous.

*Color.*—Near RHS Yellow 13A background coloration. Heavily flushed Orange-Red N30A.

Flower size:

*Diameter.*—Approximately 2.0 cm.

*Length.*—Approximately 4.0 cm.

Petals(unfused floral section):

*Length.*—Approximately 0.6 cm.

*Diameter.*—Approxiately 0.5 cm.

*Quantity.*—4 or 5.

*Texture.*—Covered in dense, pilous hairs. Hairs colored near Red 41A.

*Apex.*—Acute.

*Color.*—When opening: Outer, visible surface: Near RHS Green-Yellow 1B. Fully opened: Outer surface: Near RHS Yellow-Orange 17A. Inner surface: Near RHS Yellow 13A. Fading: Outer surface: Near RHS Yellow-Orange 17A. Inner surface: Near RHS Yellow-Orange 17A.

Perianth tube:

*Length.*—Approximately 3.4 cm.

*Diameter.*—Approxiately 1.1 cm.

*Texture.*—Outer texture highly pubescent, inner texture glabrous.

*Color.*—When opening: Outer, visible surface: Near RHS Green-Yellow 1B.

*Fully opened*.—Outer surface: Near RHS Yellow 12A. Inner surface: Near RHS Yellow 11A.

*Fading*.—Outer surface: Near RHS Yellow-Orange 17A. Inner surface: Near RHS Yellow-Orange 17A.

Floral bracts:

*Quantity*.—1 at the base of each flower, or every other flower on inflorescence.

*Shape*.—Subulate.

*Tip*.—Cirrous.

*Base*.—Clasping.

*Texture*.—Heavily pilous.

*Length*.—Approximately 0.9 cm.

*Width*.—Approximately 0.2 cm.

*Color*.—Upper surface: Near RHS Yellow-Green N144B. Lower surface: Near RHS Green-Yellow 1B.

Peduncle:

*Length*.—Average 9 cm.

*Diameter*.—0.5 cm.

*Color*.—Near RHS Greyed-Red 178A.

*Aspect*.—Straight to slightly undulating.

*Strength*.—Very strong.

*Texture*.—Farinose and pilous.

Pedicels:

*Length*.—Average 0.2 cm.

*Diameter*.—0.1 cm.

*Color*.—Near RHS Yellow-Orange 17A.

*Orientation*.—Approximately 45 degrees from peduncle.

*Strength*.—Very strong.

*Texture*.—Pilous.

Sepals not present.

Fragrance: None.

REPRODUCTIVE ORGANS

Stamens:

*Number*.—6.

*Filament length*.—Filaments are mostly fused to petals. Approximately 0.4 cm, unfused.

*Filament color*.—Near RHS Green-Yellow 1B.

Anthers:

*Shape*.—Ovoid.

*Length*.—Approximately 0.1 cm.

*Color*.—Near RHS Greyed-Oranage 167D.

*Pollen*.—Not observed.

Pistil:

*Number*.—1.

*Length*.—Approximately 3 cm.

*Style*.—Length: Approximately 2.9 cm. Color: Near RHS White 155D.

*Stigma*.—Shape: Linear. Length: Approximately 0.1 cm. Color: Near RHS Yellow-Orange 17A. Ovary Color: RHS Yellow 7A.

OTHER CHARACTERISTICS

Seeds and fruits: Not observed to date.

Disease/pest resistance: Common to cultivar.

Temperature tolerance: From approximately 0° C. to more than 40° C.

What is claimed is:

1. A new and distinct cultivar of *Anigozanthos* plant named 'Rambotasy' as herein illustrated and described.

* * * * *